(12) United States Patent
Stock

(10) Patent No.: US 10,525,227 B1
(45) Date of Patent: Jan. 7, 2020

(54) NASAL EPAP DILATOR

(71) Applicant: Kevin J. Stock, St. Louis, MO (US)

(72) Inventor: Kevin J. Stock, St. Louis, MO (US)

(73) Assignee: Stock IP Holdings LLC, St. Louis ( * ) Notice: Subject to any disclaimer, the term of this patent is extended or adjusted under 35 U.S.C. 154(b) by 547 days.

(21) Appl. No.: 15/260,573

(22) Filed: Sep. 9, 2016

Related U.S. Application Data

(60) Provisional application No. 62/216,365, filed on Sep. 10, 2015.

(51) Int. Cl.
*A61M 16/20* (2006.01)
*A61F 5/08* (2006.01)

(52) U.S. Cl.
CPC .............. *A61M 16/208* (2013.01); *A61F 5/08* (2013.01); *A61M 2210/0618* (2013.01)

(58) Field of Classification Search
CPC ........... A61F 5/08; A61F 5/56; A61M 16/208; A61M 2210/0618; A62B 18/10; A62B 23/06; C01P 2004/20
See application file for complete search history.

(56) References Cited

U.S. PATENT DOCUMENTS

| | | | |
|---|---|---|---|
| 1,256,188 A | 2/1918 | Wilson | |
| 4,220,150 A * | 9/1980 | King | A62B 23/06 128/206.11 |
| 5,895,409 A | 4/1999 | Mehdizadeh | |
| 6,270,512 B1 | 8/2001 | Rittmann | |
| 6,318,362 B1 | 11/2001 | Johnson | |
| 6,386,197 B1 | 5/2002 | Miller | |
| 6,626,172 B1 | 9/2003 | Karow | |
| 6,626,179 B1 | 9/2003 | Pedley | |
| 6,863,066 B2 | 3/2005 | Ogle | |
| 6,971,388 B1 | 12/2005 | Michaels | |
| 6,978,781 B1 | 12/2005 | Jordan | |
| 7,735,491 B2 | 6/2010 | Doshi | |
| 7,735,492 B2 | 6/2010 | Doshi | |
| 7,798,148 B2 | 9/2010 | Doshi | |
| 7,806,120 B2 | 10/2010 | Loomas | |
| 7,856,979 B2 | 12/2010 | Doshi | |
| 7,987,852 B2 | 8/2011 | Doshi | |
| 7,992,564 B2 | 8/2011 | Doshi | |

(Continued)

FOREIGN PATENT DOCUMENTS

GB 219566 A * 7/1924 ............. A62B 23/06

*Primary Examiner* — Annette Dixon
(74) *Attorney, Agent, or Firm* — Creativeventure Law, LLC; Dennis J M Donahue, III; Kevin Staed

(57) ABSTRACT

A nasal EPAP dilator is employed as an intranasal device which effect differing degrees of inhibition/easing for exhalation/inhalation. A nasal dilator incorporates an outer housing that functions as a pair of connected mirror image nasal dilators, combined with a differential-action valve mechanism modulating the airflow through the passages defined by the dilators, when inserted. The valve greatly inhibits exhalation, while opening easily to inhalation which in combination with the dilating effect is thereby eased over the absence of the nasal dilator. The nasal dilator housings include spars or a screen for structural support and a stoppage mechanism for the valves and to moderate the degree of movement of a plurality of valves so that the valves can open for inhalation, and are restrained to mostly close during exhalation.

20 Claims, 17 Drawing Sheets

(56) References Cited

U.S. PATENT DOCUMENTS

| | | |
|---|---|---|
| 8,048,102 B2 | 11/2011 | Thomas |
| 8,215,308 B2 | 7/2012 | Doshi |
| 8,235,046 B2 | 8/2012 | Doshi |
| 8,235,051 B2 | 8/2012 | Söderberg |
| 8,291,909 B2 | 10/2012 | Doshi |
| 8,302,606 B2 | 11/2012 | Doshi |
| 8,302,607 B2 | 11/2012 | Pierce |
| 8,875,711 B2 | 11/2014 | Sather |
| 9,730,830 B2 * | 8/2017 | Foley ................ A61F 5/08 |
| 2004/0255947 A1 * | 12/2004 | Martin ............ A62B 18/10 128/206.15 |
| 2006/0150979 A1 | 7/2006 | Doshi |
| 2007/0107731 A1 * | 5/2007 | Reed ................ A61F 5/08 128/206.11 |
| 2007/0277832 A1 | 12/2007 | Doshi |
| 2009/0194100 A1 * | 8/2009 | Minagi ............ A61F 5/08 128/200.24 |
| 2009/0308398 A1 | 12/2009 | Ferdinand |
| 2009/0308402 A1 | 12/2009 | Robitaille |

* cited by examiner

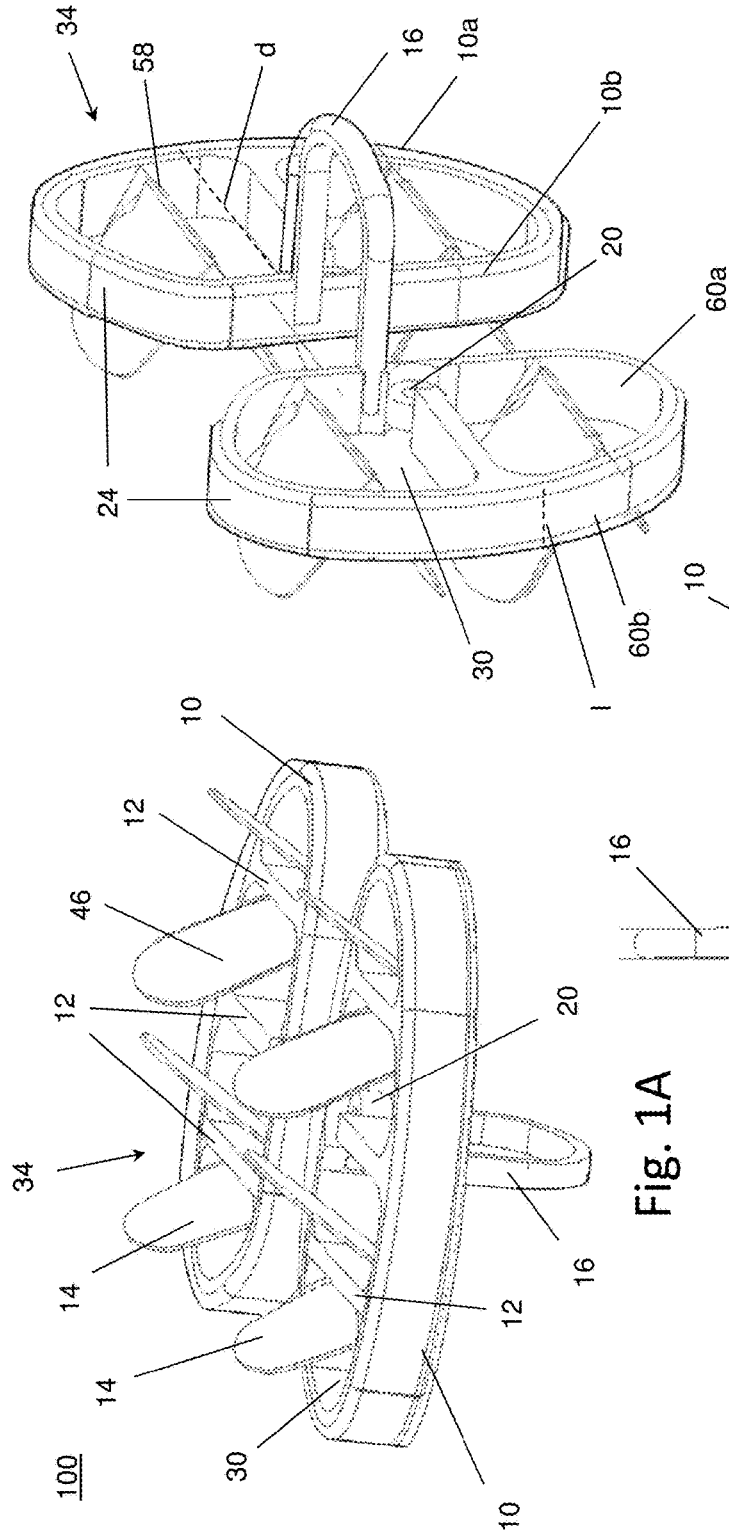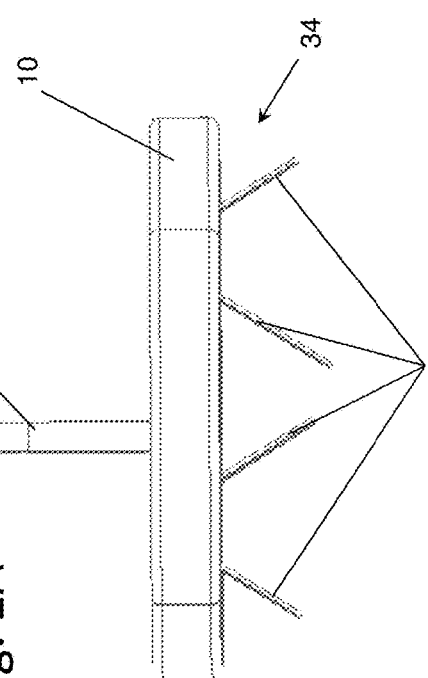
Fig. 1A
Fig. 1B
Fig. 1C

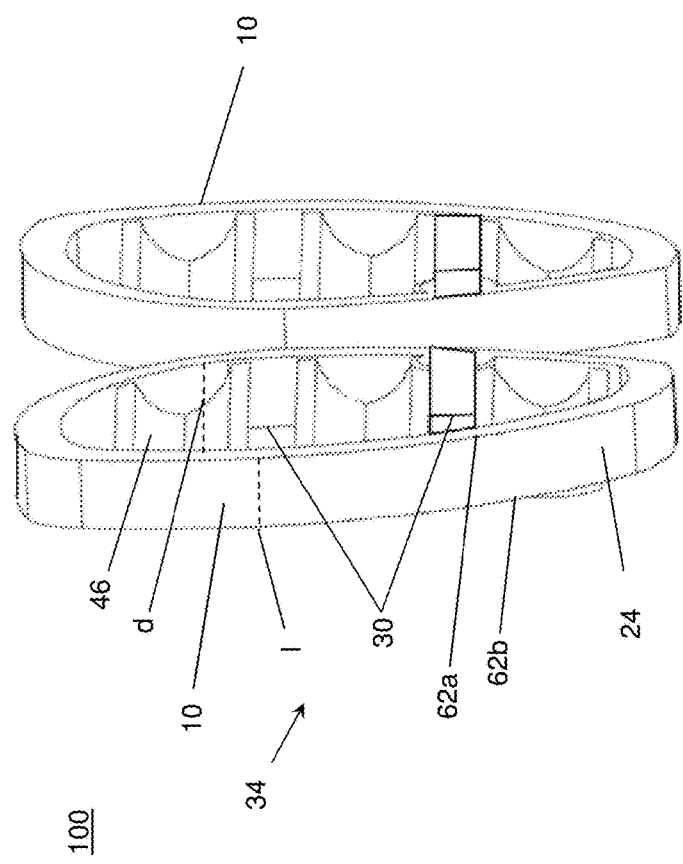
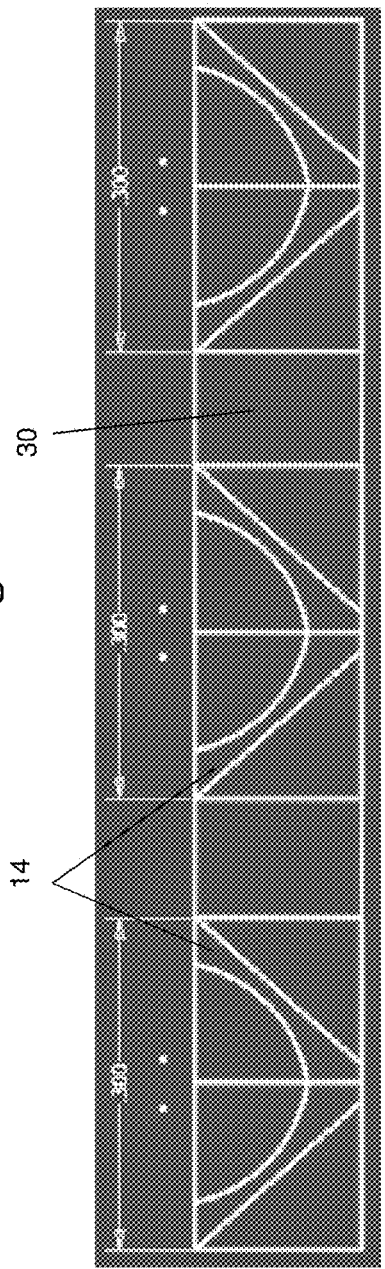
Fig. 2A
Fig. 2B

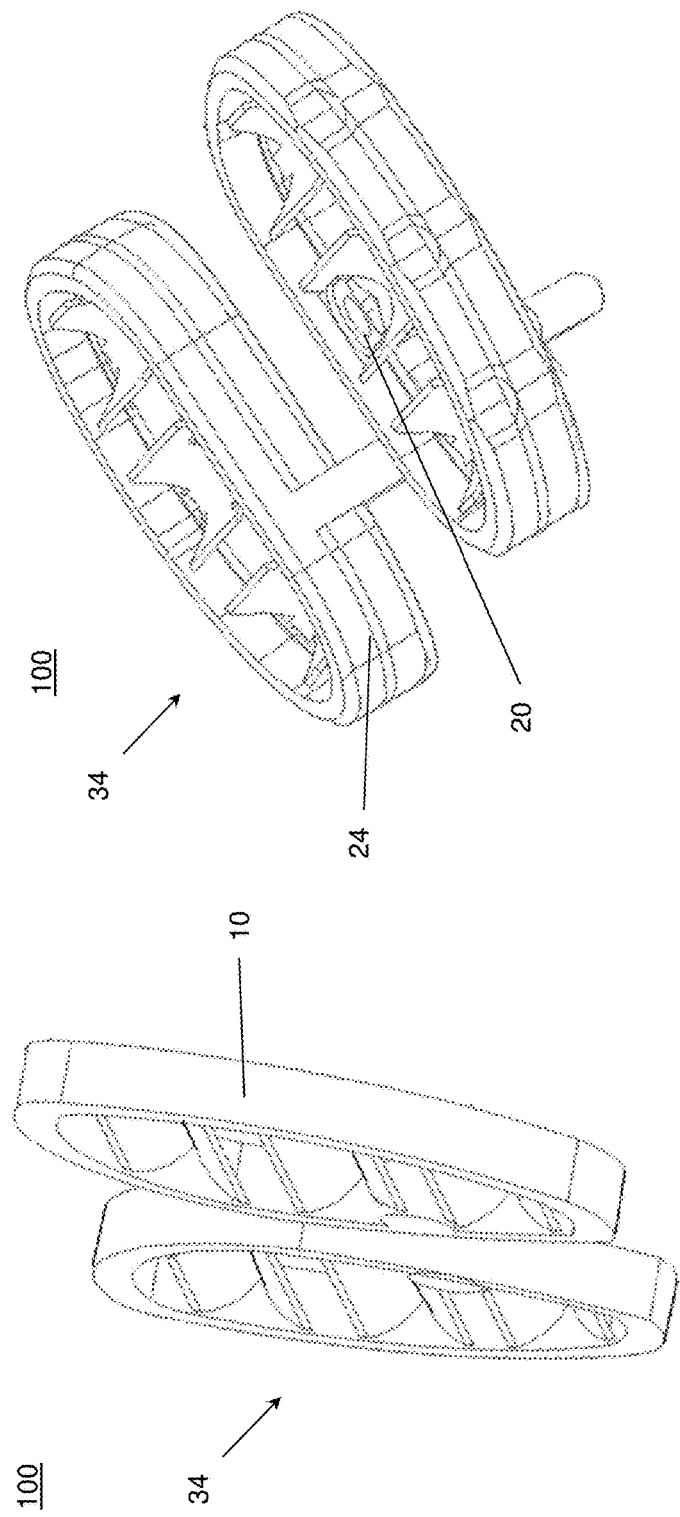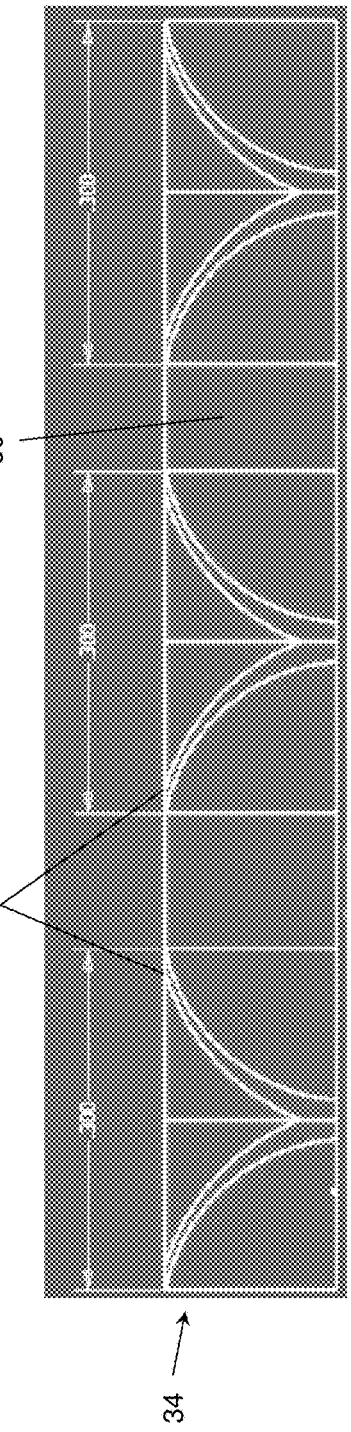

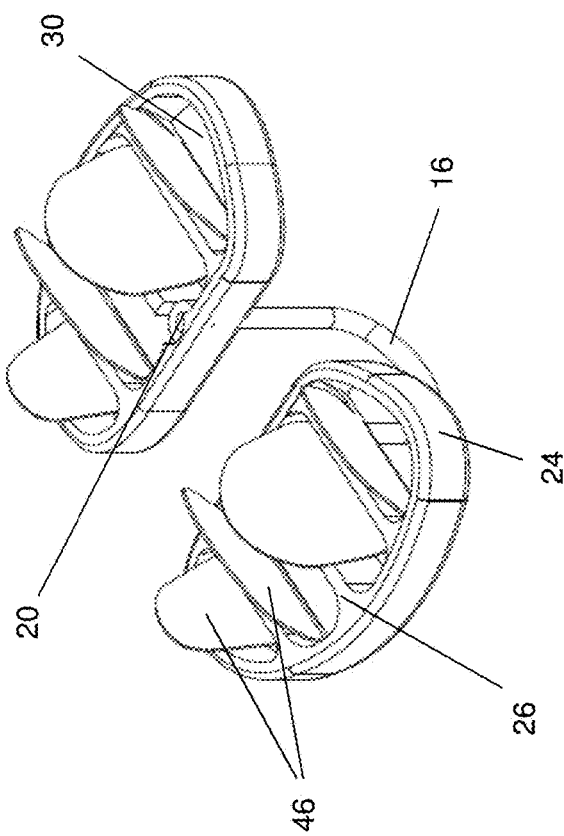
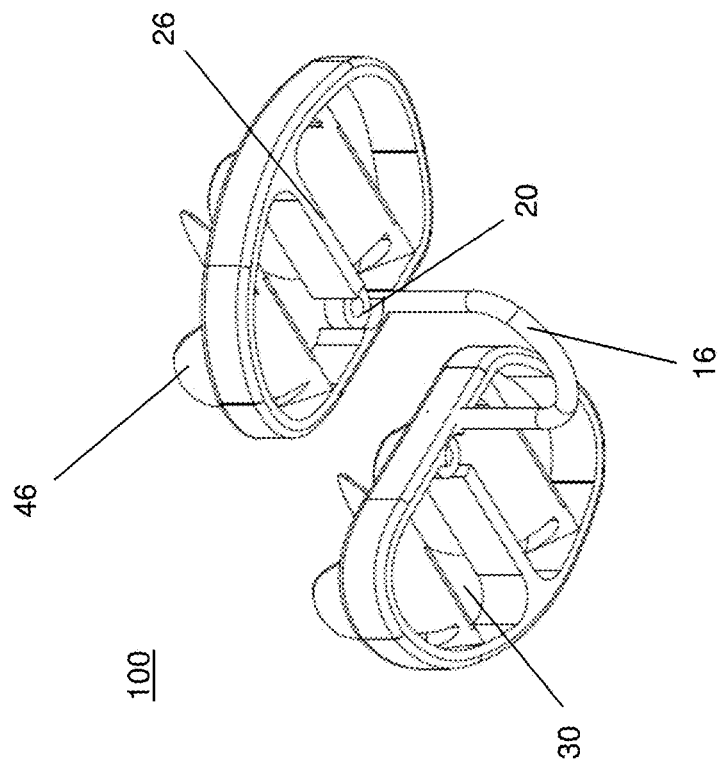
Fig. 6B
Fig. 6A

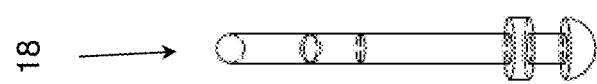
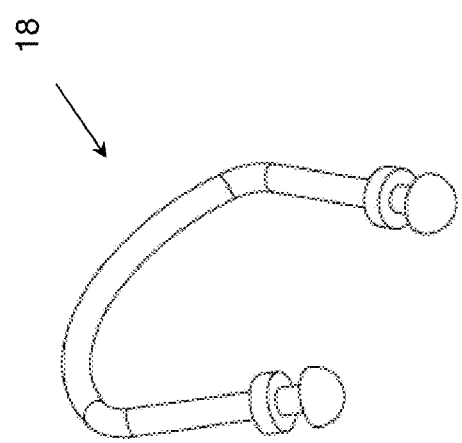

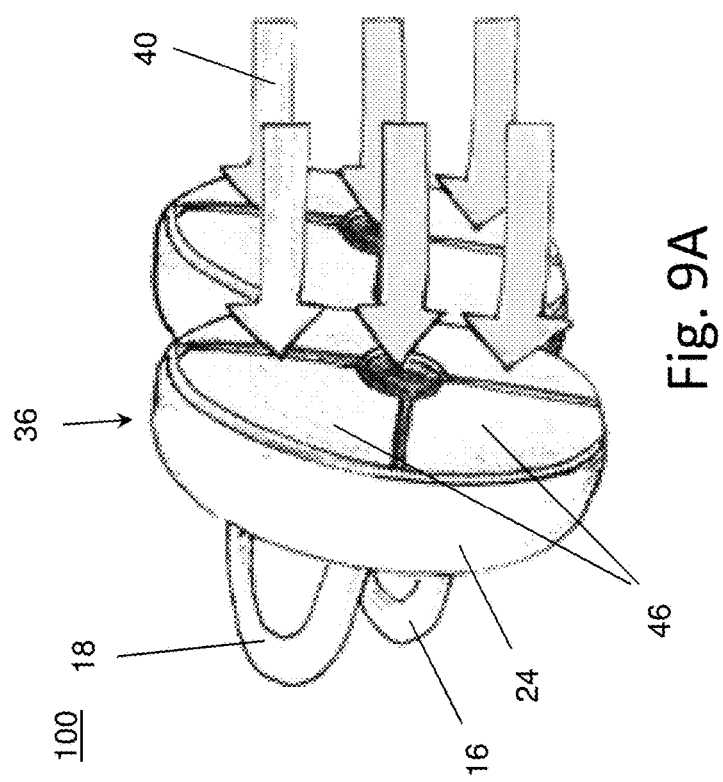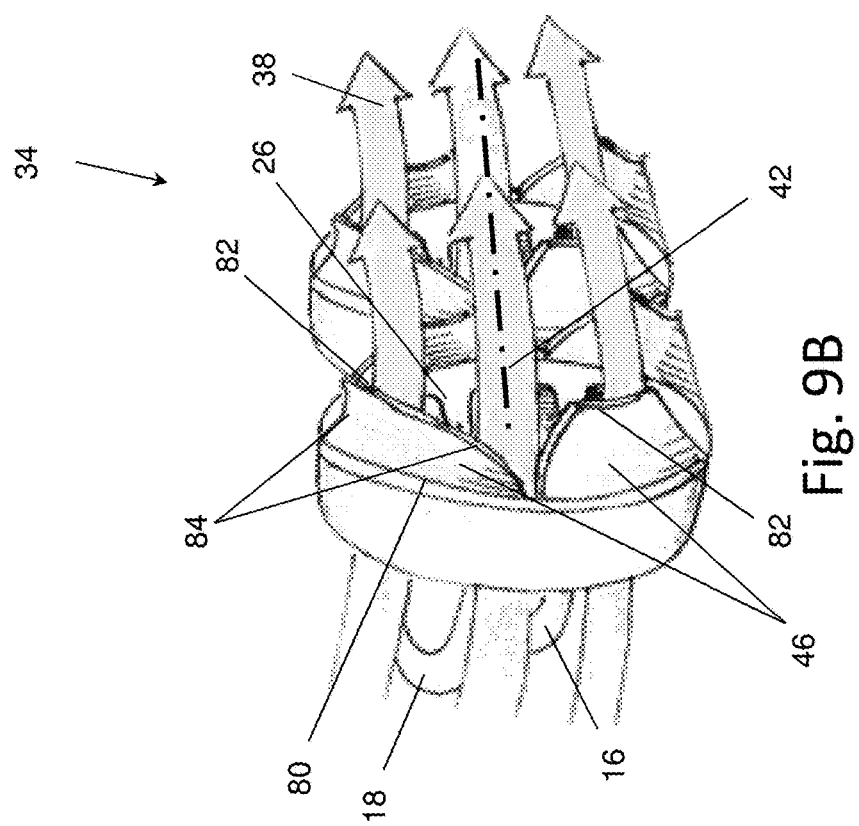

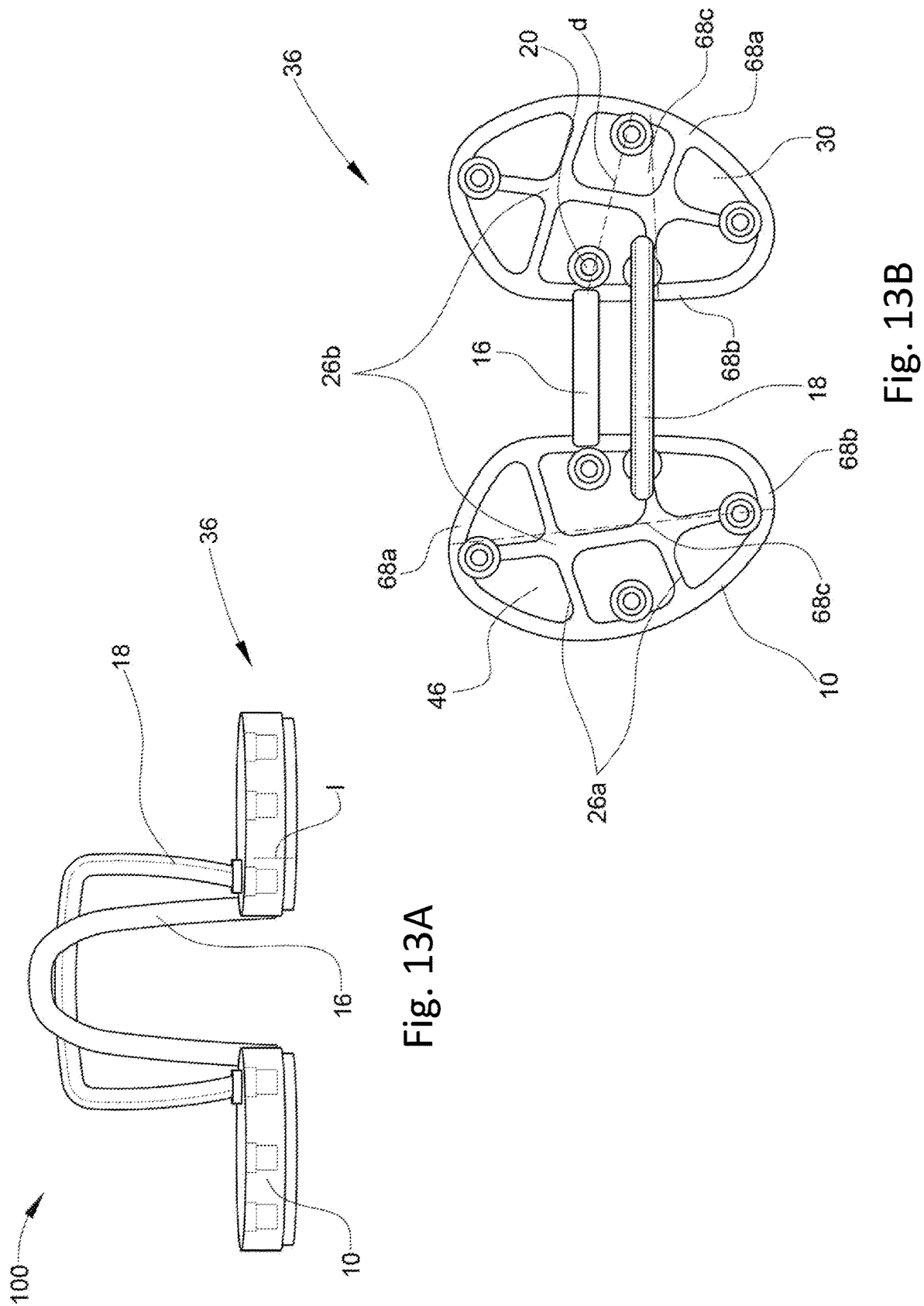

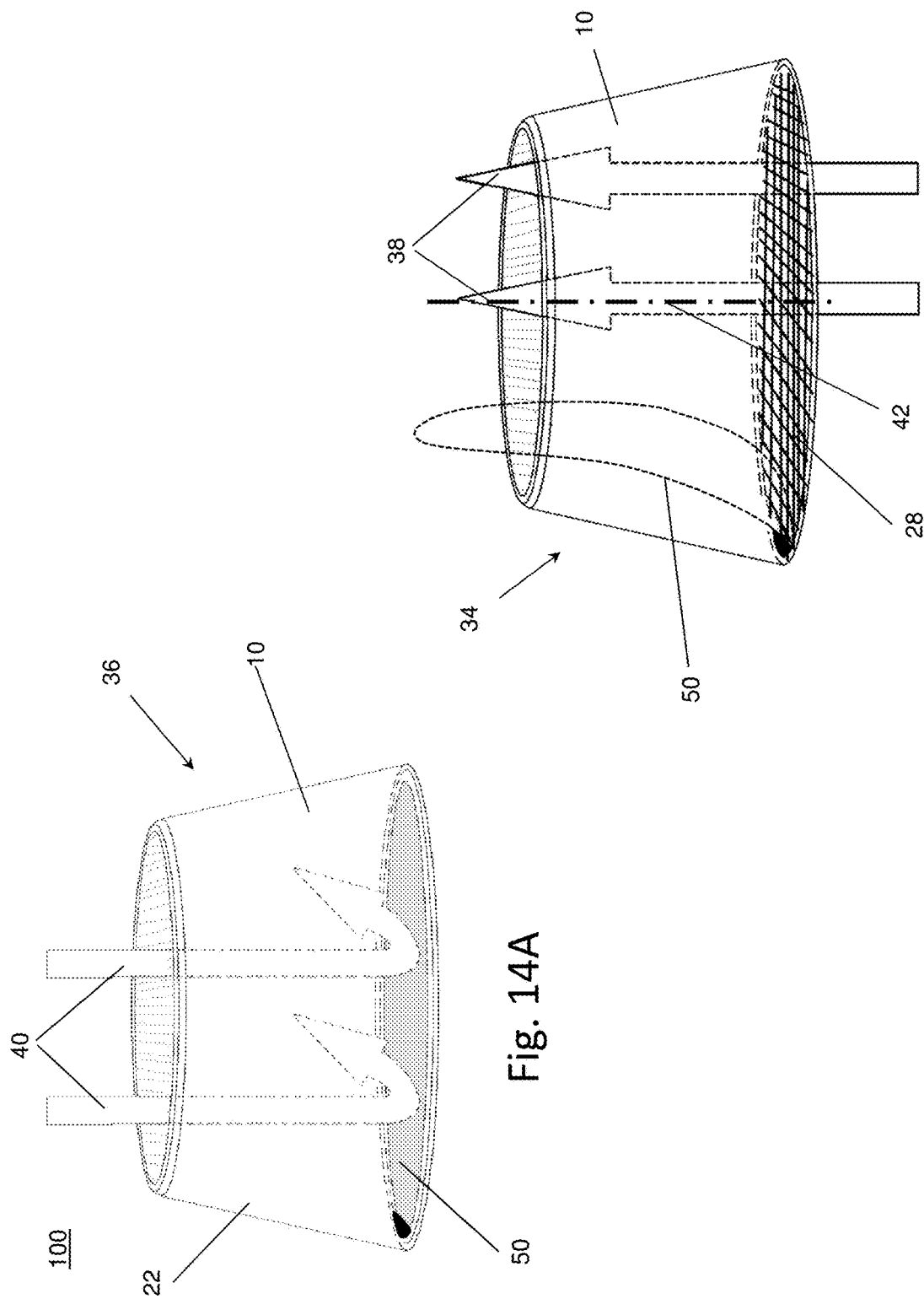

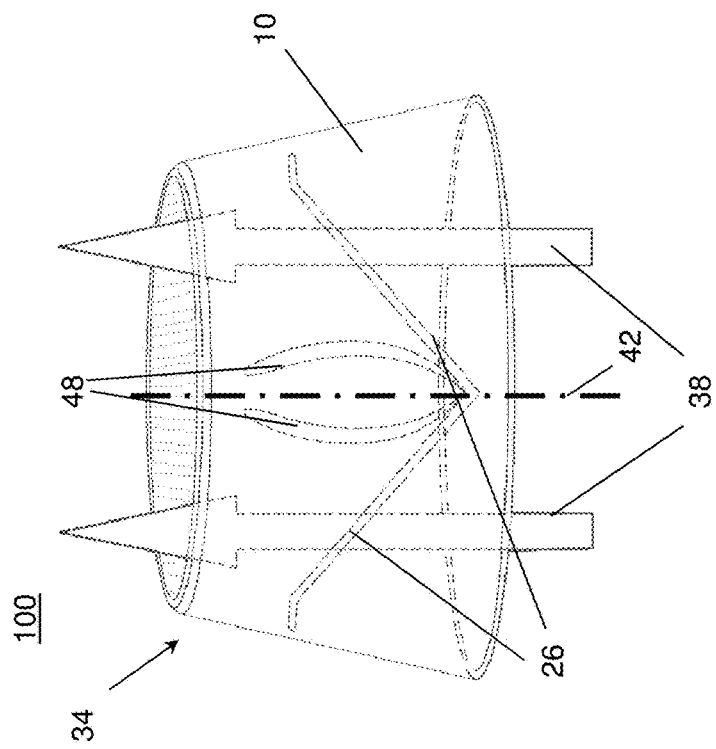
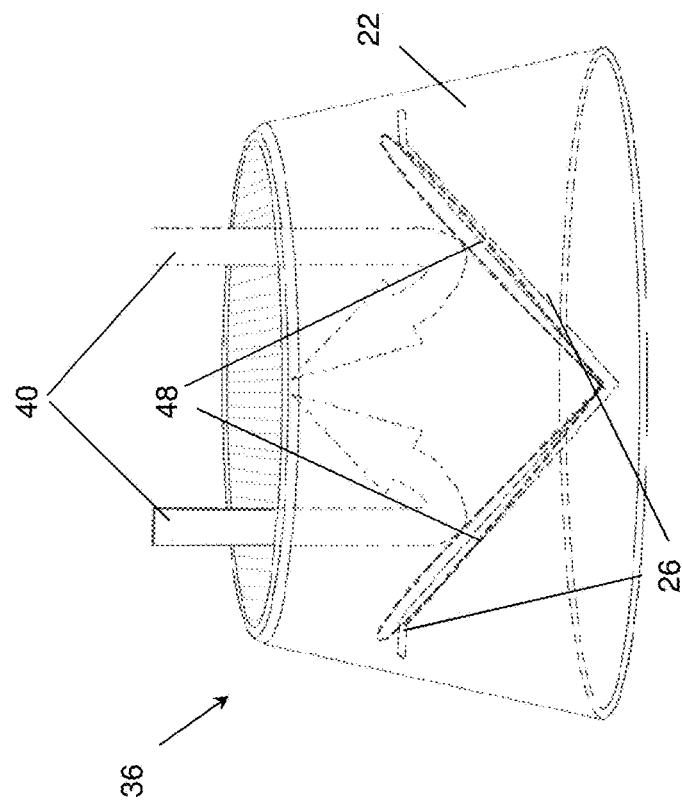
Fig. 15A
Fig. 15B

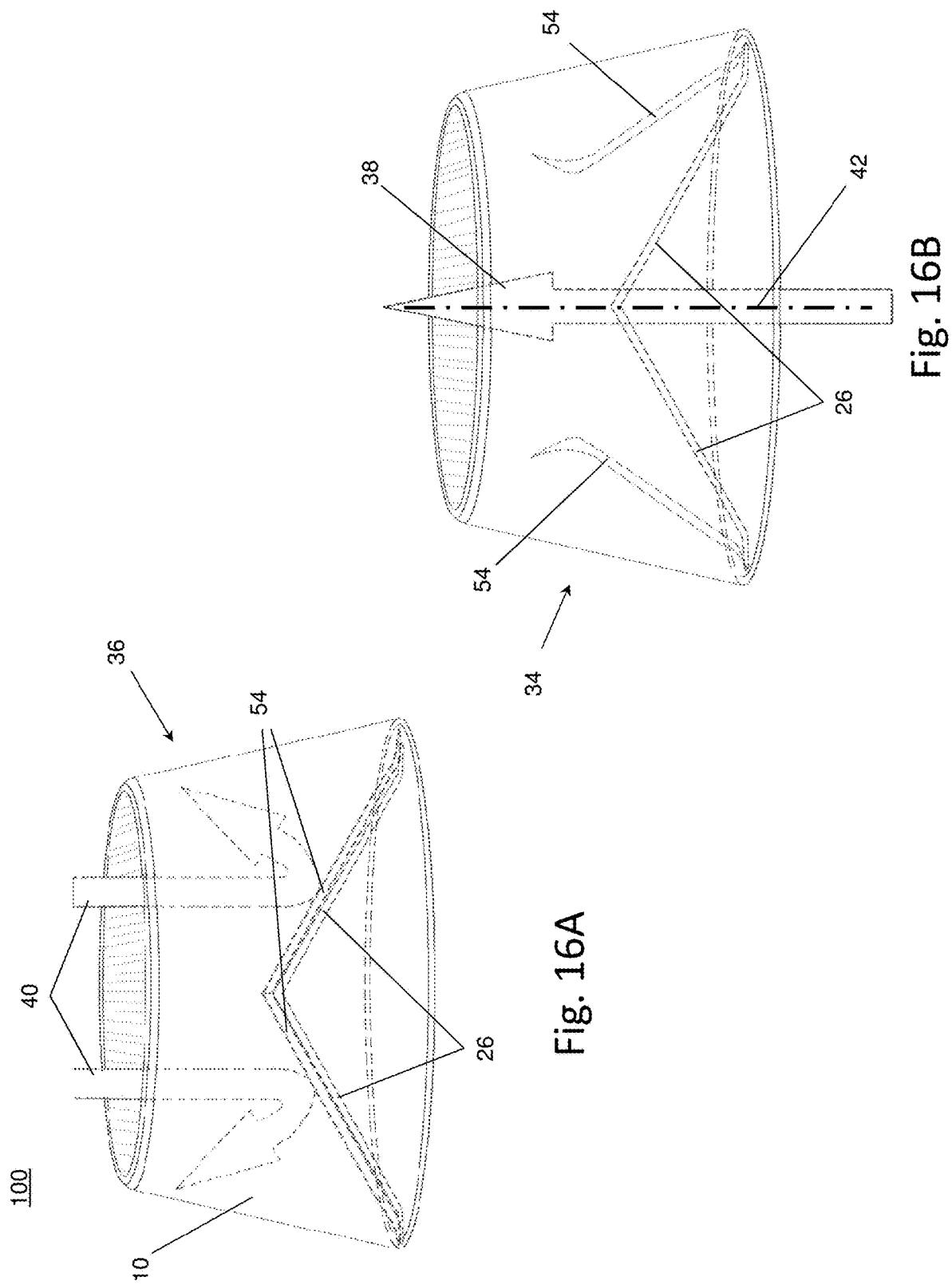

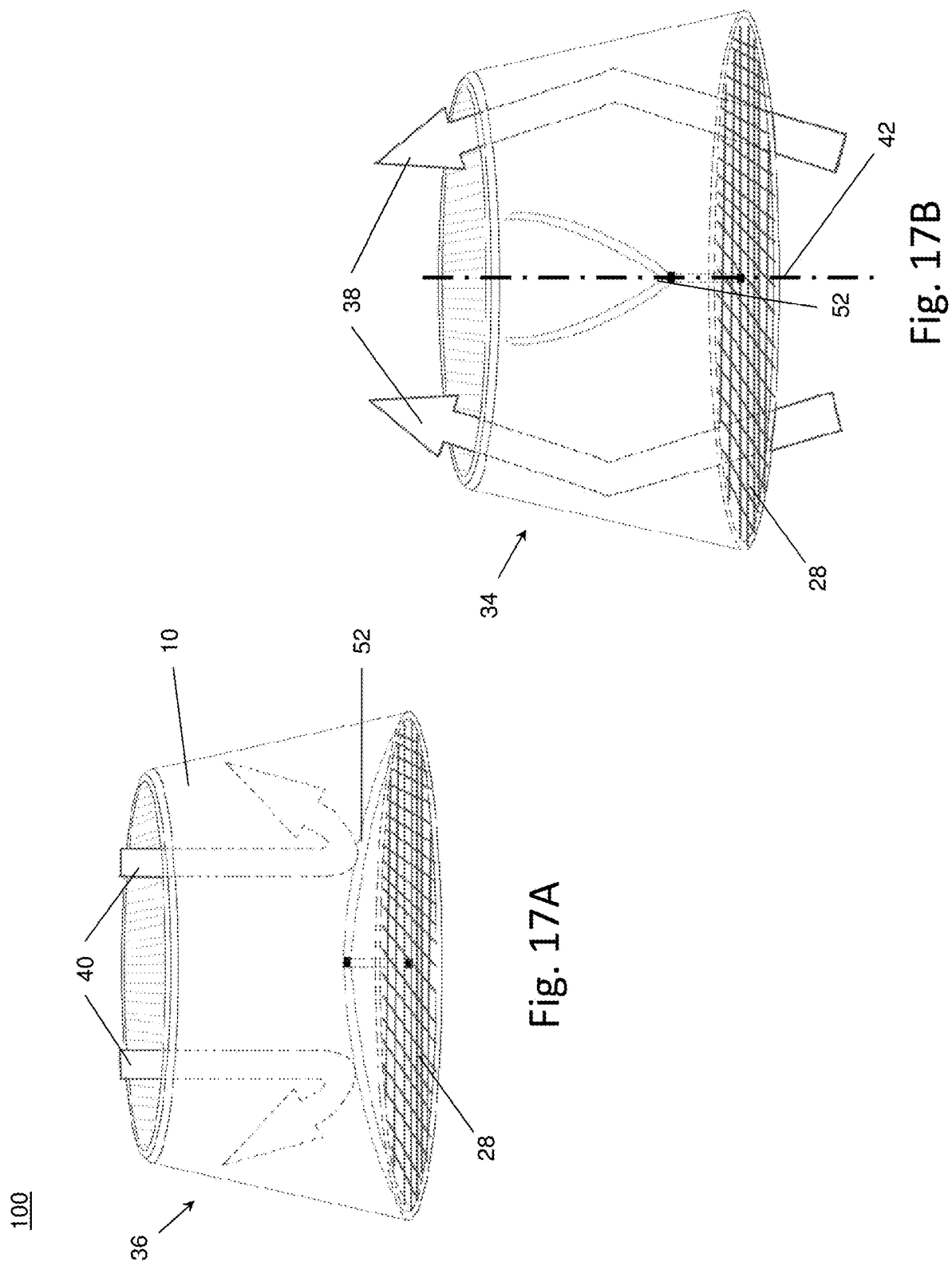

NASAL EPAP DILATOR

CROSS-REFERENCE TO RELATED APPLICATIONS

This application is a utility application claiming the benefit of provisional patent application No. 62/216,365 filed on Sep. 10, 2015, which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to nasal dilators, and more particularly to nasal dilators which reduce constriction in the nasal passageway to decrease resistance to inhalation airflow and contain a valve to increase resistance to exhalation airflow.

Related Art

A significant percentage of the population suffers from respiratory issues when sleeping, resulting in complications ranging from the mild, such as snoring, up to the major, such as sleep apnea which can become substantial enough to even contribute to a sufferer's early death. Highly effective treatments, such as continuous positive airway pressure (CPAP) are available, if the patient is compliant. Unfortunately, the devices and the difficulties involved in using them continuously have greatly reduced the efficacious employment of CPAP devices, with studies reporting that significant percentages of patients are non-adherent to treatment protocols. Clearly, effective treatment options which users find more readily usable are needed.

The term Sleep Disordered Breathing (SDB) is used to refer to a range of sleep breathing issues, such as snoring, upper airway resistance, obstructive sleep apnea (OSA). One frequent characteristic of these types of breathing-while-sleeping issues is that the internal air passages include at least some that are defined by softer mucous membranes and are subject to inhalation pressure induced narrowing as a result. While each individual varies, certain commonalities among higher risk groups have been identified and various therapies have been developed to address these commonalities. Due to the high rate of non-compliance with CPAP therapy, and frequent lack of comfort even among the compliant, alternative SDB treatments are often explored as a first treatment option. One treatment approach that has shown substantial benefit and is among the first therapy options tested is oral appliance therapy (OAT). The American Academy of Sleep Medicine (AASM) and the American Academy of Dental Sleep Medicine (AADSM) have issued guidelines for the use of oral appliances in the treatment of OSA.

There are substantial numbers and types of oral appliances available that effect OAT with a variety of approaches, due to the differences among individual users. While the degree of benefit from OAT can vary, and many are designed to be variable among differing degrees of effect, it has often enough been found that there can be a tradeoff between the degree of benefit gained and the level of comfort of the user. Since the user needs to relax and sleep through the night, the comfort level can be critical. There are differing clinical measures of OSA therapeutic effect, and on at least some occasions it has been found that when the oral device was setup with sufficient action to achieve the needed level of therapeutic effect, that the patient no longer had the comfort level needed for successful sleep. In addition, attempts to achieve greater therapeutic outcomes with OAT have shown to lead to higher risks of adverse side effects which include, and are not limited to, temporomandibular disorder (TMD), occlusal bite changes, tooth movement, headaches, and pain associated with the head and neck and other potentially long term ramifications.

It should be understood that these past, and the present invention, nasal therapies have uses beyond their combination with OAT's and that none of these uses are being disavowed for such uses. The use of a nasal therapy to "perfect", so to speak, the benefits achieved with OAT are of particular note herein and the discussion of them is also fully expository of the benefits, functions, and manners of construction/use of either the past, or the present invention's, form of nasal therapy. Most nasal therapy approaches generally attempt to use manipulation of airways and their exits/entrances to modify internal air passage pressures in manners intended to further treat SDB similar to some of the effects of CPAP devices. While much still needs to be learned, it has been generally agreed that using elevated internal air passage pressures, for at least a portion of the breathing cycle, can contribute at least partial relief for symptoms of SDB. Among the approaches to providing relatively more comfort that has been employed to raise internal air passage pressure are at least partial obstructions to exhalation. It has been found that there are still levels of improvement in wearing comfort that are desired, as well as more complex differential shaping of exhalation vs. inhalation air flow passage modifications.

There are a number of different designs for nasal therapy devices, but they do not have the beneficial features and functionality of the present invention. For example, U.S. Pat. No. 7,735,492 discloses a nasal Expiratory Positive Airway Pressure (EPAP) device with a housing and an airflow resistor. Although this device's housing can serve as a nasal dilator when no resistor is in the housing, the addition of the airflow resistor to the housing increases the resistance to inhalation airflow, and the airflow resistor increases the resistance to exhalation airflow even more than the inhalation airflow. The increase in resistance to inhalation airflow is due to the inherent stiffness of the airflow resistor that is necessary for the flap valve to provide even more resistance to the exhalation airflow and to avoid blowout of the valve during normal exhalation situations according to the design of the flap valve and housing in the '492 Patent, such as when the flap blows through its annular seat, because this design does not use any type of support structure extending across the interior space of the housing to support the flap valve.

The devices disclosed in U.S. Pat. No. 6,626,179 is for another nasal EPAP device. Similar to the '492 Patent's device, the flap valve restricting device in this invention does not have any type of support structure extending across the interior space of the housing. Therefore, the flexible flap valve embodiment must have sufficient strength that it is sufficiently supported by the annular seat so that it does not blowout during normal exhalation. The supports for the ball valve embodiment also do not extend across the interior space of the housing, and even if they did so, the ball valve necessarily causes a resistance to airflow during inhalation although its resistance can be less than the exhalation airflow resistance.

Another nasal EPAP device is disclosed by U.S. Pat. No. 9,326,885. Similar to the '492 Patent, the cannula body or housing of this device can provide a radial outward pressure so as to slightly increase the size of the nasal vestibule. However, as with the other previously known EPAP nasal devices, the diaphragm-type valve in this device restricts airflow during both inhalation and exhalation. Similar to the other previously known EPAP nasal devices, the resistance to airflow during the inspiratory phase is less than the resistance to airflow during the expiratory phase. In addition to the relative stiffness of the diaphragm valve, this device also has an anchoring stem and retaining prong on the inner end of the cannula body which extends into the housing's interior space and prevents the valve from fully opening during inhalation.

Some different types of nasal EPAP devices use stopping mechanisms to prevent blowout of flap valves. For example, U.S. Pat. Nos. 8,302,607 and 7,987,852 disclose the use of mesh or cross-bars which limit the extent to which valves can flex during exhalation and serve as a stop to blowouts. However, these devices are held in place at the exit plane of the nasal passageway by an adhesive rather than being inserted into the nasal passageway. Accordingly, these devices do not have housings that dilate the nasal passageway sufficiently to improve inhalation airflow.

Accordingly, there remains a need for a nasal EPAP device that has a valve to restrict the exhalation airflow while also improving the inhalation airflow by dilating the nasal passageway and freely allowing airflow to pass through the valve during inhalation for a net reduction in the restriction to airflow during inhalation as compared to breathing without the nasal device.

SUMMARY OF THE INVENTION

A housing of variable shape, deployed within a user's nasal passageway to create dilation. A number of flaps within the housing with open and closed configurations that restrict and promote airflow within the nasal passageway. The housing also consists of a number of spars or a screen used to provide a stop for the flaps in the closed position. The housing can be connected to another housing through a bridge connection that can be integrally formed and detachable.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings. The drawings constitute a part of this specification and include exemplary embodiments of the invention, which may be embodied in various forms. It is to be understood that in some instances, various aspects of the invention may be shown exaggerated or enlarged to facilitate an understanding of the invention; therefore the drawings are not necessarily to scale. In addition, in the embodiments depicted herein, like reference numerals in the various drawings refer to identical or near identical structural elements.

FIGS. 1A-1C are perspective and side views of a nasal dilator with flap valves in a planar frame housing.

FIGS. 2A and 2B are a perspective and schematic view, respectively, of a nasal dilator with concave flap valves.

FIGS. 3A and 3B is a cross-sectional view and a schematic view, respectively, of a nasal dilator with convex flaps.

FIG. 4 is a perspective view of a nasal dilator with curved flap valves.

FIGS. 6A and 6B are bottom and top perspective views, respectively, of a nasal dilator with flap valves.

FIGS. 7A and 7B are a perspective view and a side view, respectively, of the detachable bridge.

FIGS. 9A and 9B are schematic depictions of the nasal dilator with a multi-flap valve during exhalation and inhalation, respectively.

FIGS. 13A and 13B illustrate a side view and a bottom view, respectively, of the nasal dilator with a longitudinal spar intersecting with the lateral spars.

FIGS. 14A and 14B are schematic views of a nasal dilator with a hinged disc valve and screen during exhalation and inhalation, respectively.

FIGS. 15A and 15B are schematic views of a nasal dilator with a diaphragm valve and angled spars during exhalation and inhalation, respectively.

FIGS. 16A and 16B are schematic views of a nasal dilator with a duck valve and angled spars during exhalation and inhalation, respectively.

FIGS. 17A and 17B are schematic views of a nasal dilator with an umbrella valve and a screen with a central post during exhalation and inhalation, respectively.

DETAILED DESCRIPTION OF THE PREFERRED EMBODIMENTS

The following description of the preferred embodiment(s) is merely exemplary in nature and is in no way intended to limit the invention, its application, or uses.

Figure 8B:
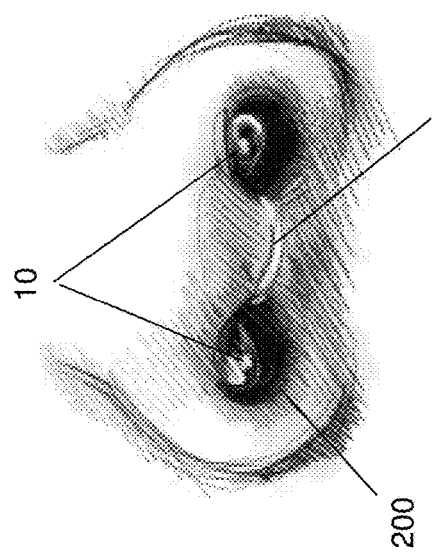
FIGS. 8A-8C are perspective, front and side views of the nasal dilator inserted within a user's nasal passageway.
Figure 8C:
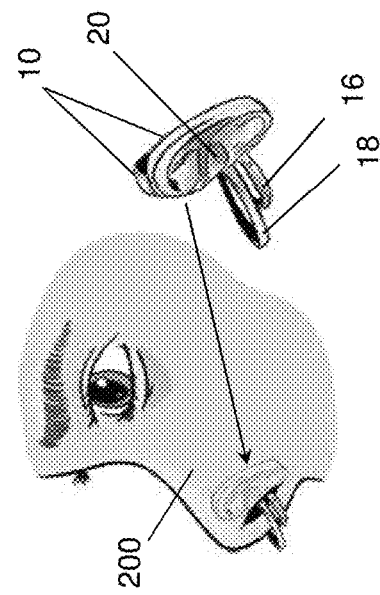
Figure 8A:
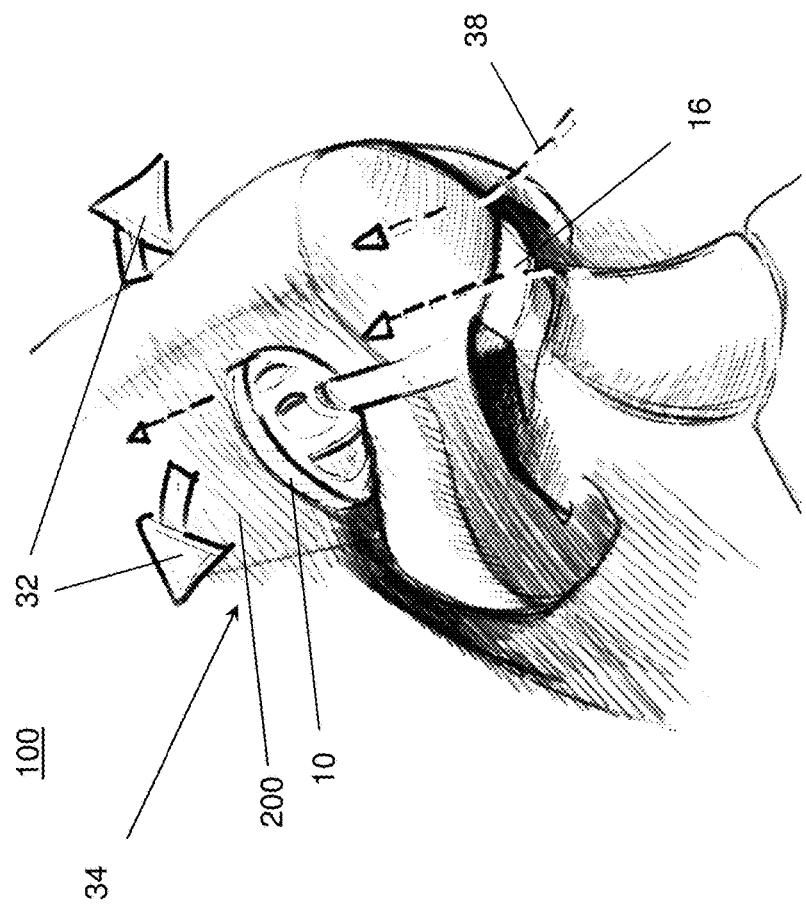
Figure 10B:
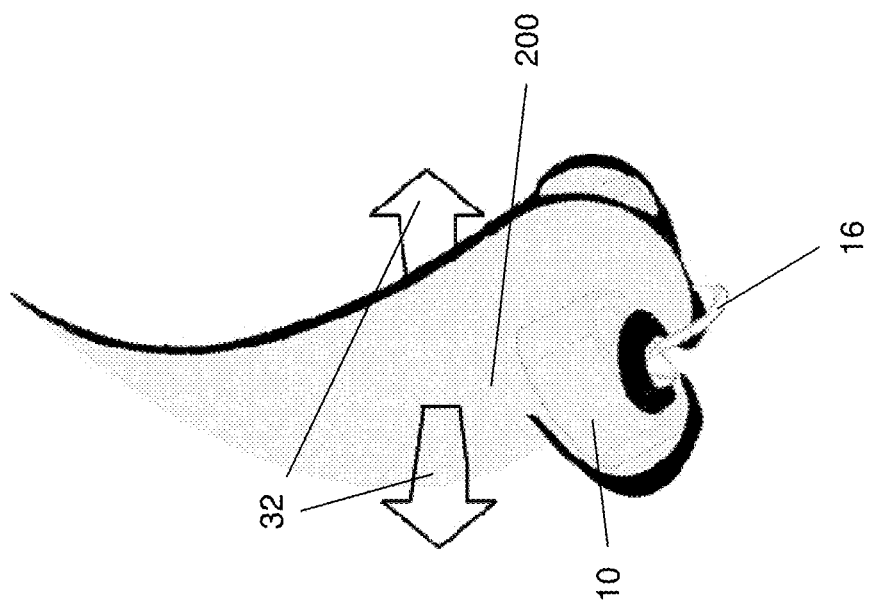
FIGS. 10A and 10B are perspective views of the nasal dilator with an elongated housing before installation and while inserted within a user's nasal passageway, respectively.

As generally shown in FIGS. 1-18, a nasal EPAP dilator (NED device) 100 has a housing 10, a seat 12 that is connected to the housing's opposing sidewalls 10a, 10b and spans the housing's interior space 30, and a valve 14 that is situated toward the inner side of the seat. The housing has an interior surface 60a, an exterior surface 60b, an inner end 62a and an outer end 62b. The seat is closer to the outer end of the housing than the valve, i.e. the seat is on the outer side of the valve, so that the seat provides support to the valve during exhalation 40 and prevents a blowout of the valve during exhalation. The housing's 10 exterior surface 60b is shaped to fit within a user's nasal passageway and expands the nasal passageway to create a dilation 32 that is of sufficient strength to prevent the outer edges of nares from collapsing inwardly toward the nasal septum during inhalation 38, preventing or otherwise counteracting constriction during inhalation. During inhalation, the valve 14 is in its open configuration 34, opening toward the housing's inner end, allowing air to flow freely through the dilated nasal passageway 56a. FIGS. 8A and 10B depict the NED device disposed as when in use with the dilation 3, with the dilating effect, effectively assisting inhalation by the user. During exhalation, the valve 14 is in its closed configuration 36 and is positioned against the seat 12. In the closed configuration, a back pressure is created while a small amount of air flows through the valve and out of the nasal passageway.

The shape of the housing 10 for the NED device 100 can vary to satisfy a range of shapes of nasal passages. According to the various embodiments described below, it will be appreciated that many different types of valves 14 can be used, such as a flap valve 46, a diaphragm valve 48, a hinged disc valve 50, an umbrella valve 52, and a duck valve 54. Additionally, according to the different embodiments, the seat 12 may be formed from spars 26, a screen 28, or any structural support that is connected to the housing's opposing sidewalls and spans the housing's interior space. For an oblong shaped housing, the spars 26 can be lateral spars 26a that span the shorter length of the interior space and/or longitudinal spars 26b that span the longer length of the interior space 30, such as shown in FIG. 13B. Preferably, the seat and valves are integrally formed with the housing, but they may also be formed separately and be connected by a mechanical means, such as a separate mount or an adhesive layer, or may be fused together, such as by heating.

The valve 14 is preferably formed from a flexible flap that may be integrally constructed with the housing 10 and spars 26 from the same flexible material. The flap membrane material can be sufficiently thin to readily curl, fold, or otherwise moved to open away from the seat during inhalation, whereas the thickness of the material for the housing and the spars are preferably sufficient to provide support for the dilation of the nasal passageway. In some cases, the valves 14 will be formed with predetermined resting configurations that incorporate curved topographies and/or ellipsoid cross-sections in order to facilitate one or more of opening the valves 14 during inhalation, and closing the valves 14 during exhalation 40. In addition to folding or bending, the operation of the flaps can also be enacted with hinged mounts; folding corrugations; apertures sliding on guidelines, rings, or wires; and other similar basic forms of pivoting interconnections. The materials used to form the NED device can be silicone, plastic, latex, or any other compound suitable for intranasal use and having the performance characteristics desired for freely flowing inhalation airflow and restricting exhalation airflow, and may be a thermoplastic material.

Figure 19:
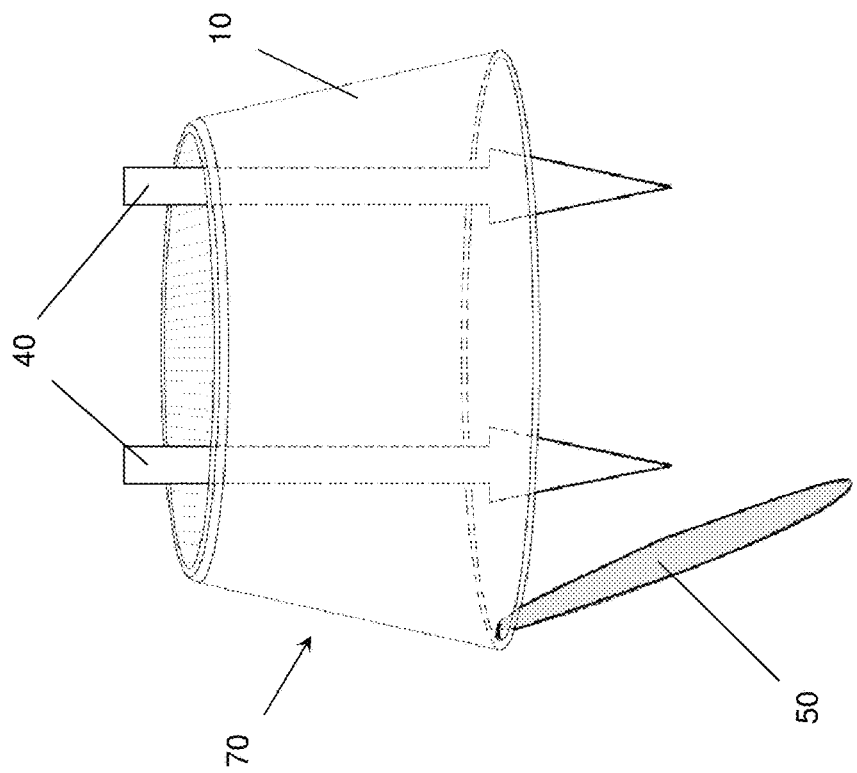
FIG. 19 is a schematic view of a prior art EPAP device with a flap valve having an annular seat support but without a seat support spanning the housing interior space allowing the blowout of the flap valve.

Depending on the configuration of the valve 14 and the housing 10 and the connection between the valves and housing, the valve material may be formed from a more rigid material, such as substantially rigid plastic that may be connected by very flexible hinges. Again, the particular combination of materials for the valve, housing, and seat and their respective arrangements relative to each other should provide for freely flowing inhalation airflow and restricting exhalation airflow. With regard to the arrangement of the valve, housing, and seat, the seat 12 is connected to and situated toward the outer end of the housing to provide a stopping mechanism for the valve 14. The seat is on the outer side of the valve to prevent a blowout 70 of the valve 14 that is possible with the prior art, such as shown in FIG. 19 in which the valve is forced past the outer end of the nasal EPAP's housing. Accordingly, for the nasal EPAP dilator (NED) of the present invention, the seat allows the valve to be flexible enough so that it allows air to flow freely during inhalation and provides the support to the valve during exhalation to ensure that the valve provides the EPAP back pressure for the NED device 100. It will be appreciated that the spars 26 also provide structural support to the housing that helps with the dilation of the nasal cavity.

Generally, the NED device 100 will include two housings 10 to be used in both nasal passageways of a user. The housings 10 can be used by themselves or can be connected by one or more bridges 16, 18 that serve to maintain the orientation and pairing of the two housings 10. The bridge can also serve to help in the dilation of the nasal passages and may provide for convenience during manufacturing. The bridge also simplifies the usage of the NED device by providing a gripping portion that remains outside of the nose that helps in inserting the NED device into the nasal passageway and also helps in the removal of the NED device from the nasal passageway. A flexible bridge 16 that may be formed integrally with the housing and a more rigid bridge 18 may be formed separately from the housing and connected to the housing through bridge receivers 20 that are formed as a part of the housing. The receivers 20 allow a detachable bridge 18 to be inserted and secured in a disposition roughly similar to that of the bridge 16.

Figure 10A:
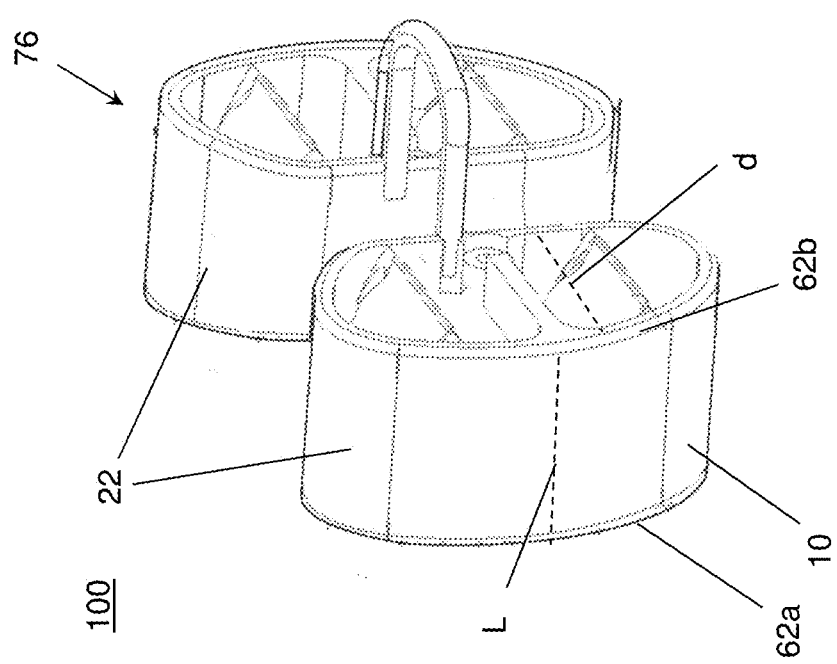
Figure 11:
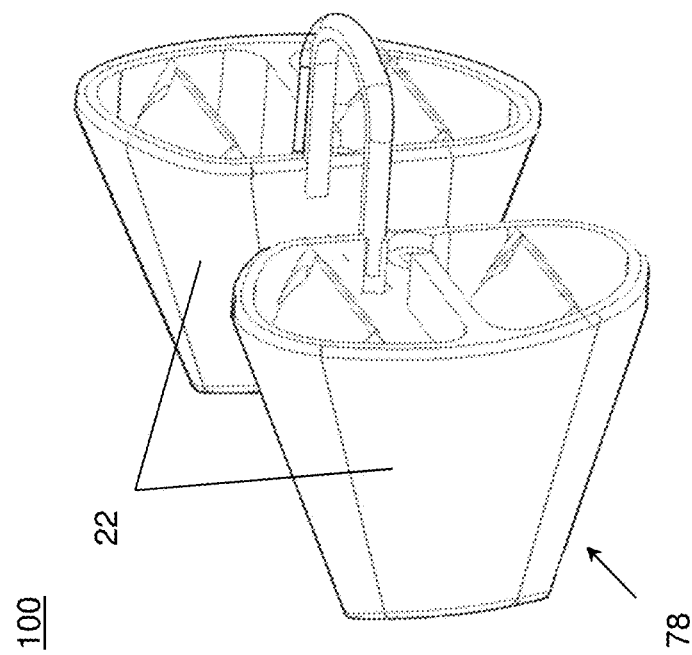
FIG. 11 illustrates the nasal dilator with a cone shape housing.

The housing 10 can be an elongated tube 22 or a planar frame 24. In the elongated tube 22 embodiments, the length (L) between the inner end of the housing and the outer end of the housing is longer than the distance (d) between the housing's opposing sidewalls 10a, 10b (L>d) as shown in FIG. 10A. In the planar frame 24 embodiments, the length (l) between the inner end of the housing and the outer end of the housing is either equivalent to or shorter than the distance (d) between the housing's opposing sidewalls 10a, 10b (l≤d) as shown in FIG. 2A. In the elongated tube 22 embodiments, the housing 10 can be either conical 78, such as shown in FIG. 11, or cylindrical 76, such as shown in FIG. 10A.

FIGS. 1A-1C depict an embodiment of the NED device 100 with flaps 46 of the valve disposed in an open configuration 34 that will allow inhalation airflow 38 to pass through the interior space 30. In passing through the NED device, the inhalation airflow moves the flaps 46 into a more open configuration 34. The flaps 46 meet at their wider ends at a juncture 58 which is interconnected with the housing 10. The juncture 58 can be constructed in a variety of ways, according to how the flaps 46 are constructed, and the design objectives of a particular embodiment. In this first embodiment, the flaps 46 are relatively stiff, so that the construction of the juncture 58 results in the free movement of the flaps 46. The juncture can be constructed as a hinging or folding articulation, or of a substantially flexible material such as silicone, among other variations. An instance of the first embodiment includes a pair of housings 10 which are generally not symmetrical, since they are designed to at least generally conform to the nasal passage's internal topography. A plurality of spars 26 extend across the shorter reaches of the housing 10 to span the housing's interior space. The spars also provide structural support to the housing 10 and prevent a blowout of the flaps 46 so that the flaps 46 are pressed against and stopped by the spars 26 during exhalation. While many of the embodiments of the present invention use a series of spars in each mirror image dilator, it is also within the scope of the present invention for a single spar to be used. Other embodiments show how the flaps 46 may differ in size, shape, number, orientation, and manner of operation.

Further variations of other aspects of the present invention are depicted in the partial perspective schematic views of a concave flap cross-section embodiment, as shown in FIGS. 2A and 2B, and a convex flap cross-section embodiment, as shown in FIGS. 3A and 3B. In these two embodiments, the cross-section construction of the flaps 46 is varied, both to manipulate the properties of the flaps' 46 surfaces interactions with the airflow passing through the interior space 30 defined by the housing 10, as well as to manipulate how the flaps 46 would bend or fold, when they are flexibly constructed. The convex flap embodiment depicted in FIGS. 3A and 3B is analogous to the concave flap cross-section embodiment in FIGS. 2A and 2B, with the variation that a plurality of flap faces are convexly configured, meeting in pairs at crossing lines.

FIG. 4 illustrates a variation of the NED device 100 with curled flaps 46. The curled flaps 46 are constructed of a relatively steady thickness, preferably as thin as is effective, since the curled flaps 46 are designed to operate the differential effect of assisting inhalation airflow 38 while blocking exhalation airflow 40 by flexibly deforming in response to the air flow. The side of the housing 10 shown directed upward in FIG. 4 in use is disposed within the nasal passage facing inward, in the direction of inhalation airflow 38. The outer portions of the curled flaps 46 increase in curvature when deformed by the inhalation airflow 38 thereby further opening the airflow passages, and are flattened and deformed by their curved topography catching the exhalation airflow 40 so that their outer portions will come to a closed configuration 36.

Figure 5B:
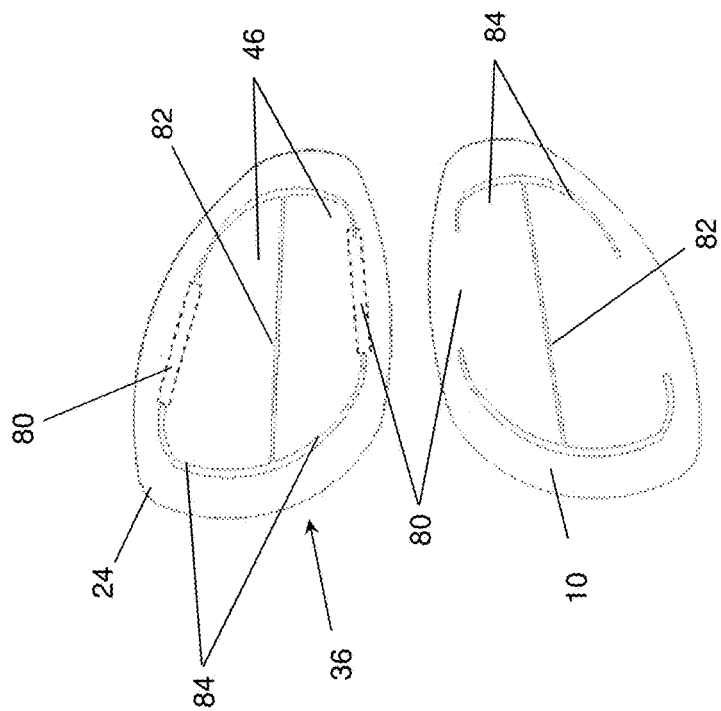
FIGS. 5A and 5B are bottom and top perspective views, respectively, of a nasal dilator with bi-flap valves.
Figure 5A:
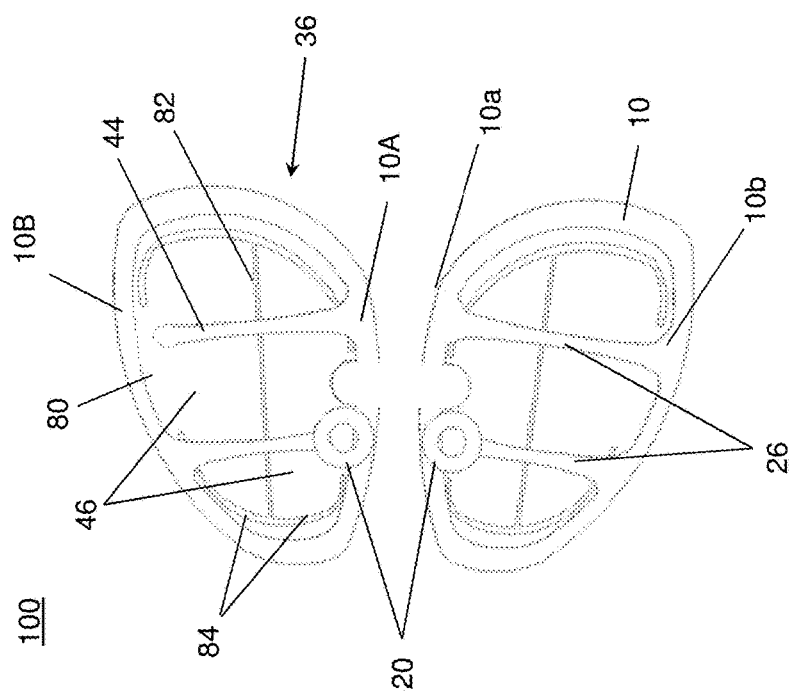

A bottom view and top view of the bi-flap embodiment, in a closed configuration 36, are shown in FIGS. 5A and 5B, respectively. Generally, the flap valves have a fixed end 80 that are connected to the housing's sidewalls. The flaps 46 of the flap valves can move freely at a free end 82 by a pair of sides 84 that extend from the fixed end to the free end. Preferably, the sides of the flaps have a curvature conforming to the shape of the interior surface of the housing. Alternative bi-flap embodiments are not shown, but are similar to the longer bi-flap embodiment, differing primarily by variations in the orientations of the flaps 46 and spars 26. FIG. 5A also shows an example of a partial spar 44 that is connected to the housing 10 only at one end and extends across the interior space to prevent the blowout of the valve. Partial spanning spars or screens can provide more flex to the housing that may provide additional comfort and fit in the nasal passageway. Additionally, partial spanning spars or screens can have other potential benefits, including but not limited to, manufacturing, function, and customizability to nasal passageways.

The detachable rigid bridge 18 is depicted in a perspective view in FIG. 7A and in a side view in FIG. 7B. The rigid bridge 18 is often constructed separately from the rest of the NED device 100, and hence is shown separately, but it should be understood that in use, the detachable bridge 18 will usually be fully integrated with the rest of the nasal EPAP dilator 100 by being inserted in the receiver 20. The bridge is generally flat in profile, with a curved center region and straighter end regions. The bridge can be stretched and narrowed to configure to differing widths of nasal passages and adjusted to optimize fit as well as aiding in the stabilization of the housing and dilation of the nasal passages.

FIG. 8A illustrates a perspective view of the planar frame NED device 100 as it is installed to produce the dilation 32 of the nasal passageway 200. FIG. 8B is a front view of the NED device as it is installed with the bridge 16 between the housings 10. FIG. 8C illustrates a perspective view of the planar frame NED device 100 with a flexible bridge 16 that is integrally formed with the pair of housings 10 and a more rigid bridge 18 that connected to the housings through the receiver 20 in each of the housings.

FIGS. 9A and 9B illustrate the airflow through the NED device 100 during inhalation and exhalation. During inhalation, the inhalation airflow 38 causes the valve 14 in the NED device 100 to operate in its open configuration 34 away from the seat 12. In this particular embodiment, the airflow forces the free end of the flaps 46 off of and away from the spars 26. The dilation produced by the housing during inhalation results in an increased airflow as opposed to airflow without the use of the NED device. FIG. 9A shows the exhalation airflow 40 during exhalation with the valve 14 in its closed configuration 26 forced onto the seat 12. The airflow pushes the flaps 46 onto their respective spars 26 and the housing provides a seal with the nasal passageway around the periphery of its exterior surface, thereby decreasing the amount of air allowed through the NED device and out of the nasal passageway and providing a backpressure in the nasal cavity and airway.

For valves which use flexible flaps 46, such as in the embodiment illustrated in FIGS. 9A and 9B and alternative embodiments described in detail below, the flexibility of the flaps is sufficient that when the inhalation airflow pushes the flaps open, the sides 84 curve toward the inner end of the housing 10 from their fixed end 80 to the free end 82. The housing has a central longitudinal axis 42 between its inner end and its outer end, and the flaps preferably have sufficient flexibility that the free end is aligned with or nearly aligned with the axis when the flaps are pushed open by the inhalation airflow.

Figure 12:
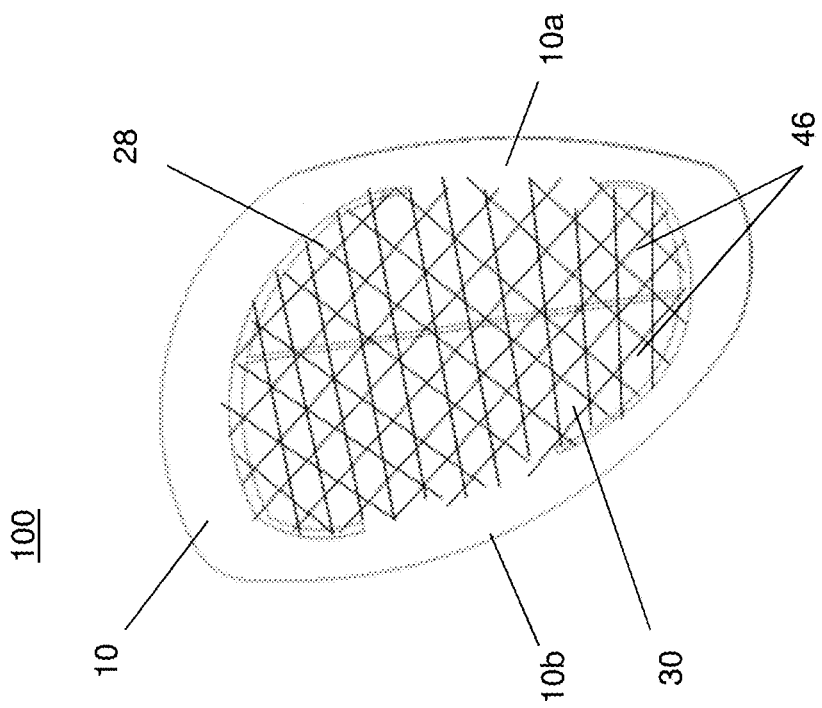
FIG. 12 illustrates the nasal dilator with a screen supporting the flap valves.

FIGS. 10A, 10B, and 11 show the NED device 100 in an alternative configuration in which the housing is an elongated tube 22. The tube shape in FIG. 10A is uniform in size of the interior space throughout, while the embodiment shown in FIG. 11 is more of a cone shape. FIG. 10B also shows how the device creates a dilation 32 of the nasal passage when in use. As shown in FIGS. 10 and 11, the seat can be formed from spars 26. Similarly, the seat can be formed from a screen 28 as shown in FIG. 12.

The embodiment of the NED device shown in FIGS. 13A and 13B has a seat that includes both lateral spars 26a and longitudinal spars 26b. The longitudinal spars intersect with the lateral spars providing further support for the housing 10 and the valves 14. This particular embodiment uses flaps 46 for the valves. The lateral spars 26a span across the shorter distance 66c between lateral opposing walls 66a, 66b of the housing 10, whereas the longitudinal spars 26b span between the longitudinal opposing walls 68a, 68b at the longer distance 68c. It will also be appreciated that diagonal spars could be used such that they span the interior space of the housing similar to the screen shown in FIG. 12.

FIGS. 14-18 illustrate alternative embodiments of the NED device 100 using a variety of valves 14. FIG. 14A and 14B display an embodiment using a hinged disc valve 50. In the closed configuration 36, the hinged-disc valve 50 restricts the exhalation airflow 40 during exhalation creating a backpressure. The hinged disc valve 50 is prevented from the blowout condition by the screen 28, which is visible in the open configuration 34 shown in FIG. 14B. FIG. 14B also shows that the hinged disc valve 50 can bend and conform to the interior of the housing 10 to allow the inhalation airflow to freely pass through the interior space of the housing.

Figure 18:
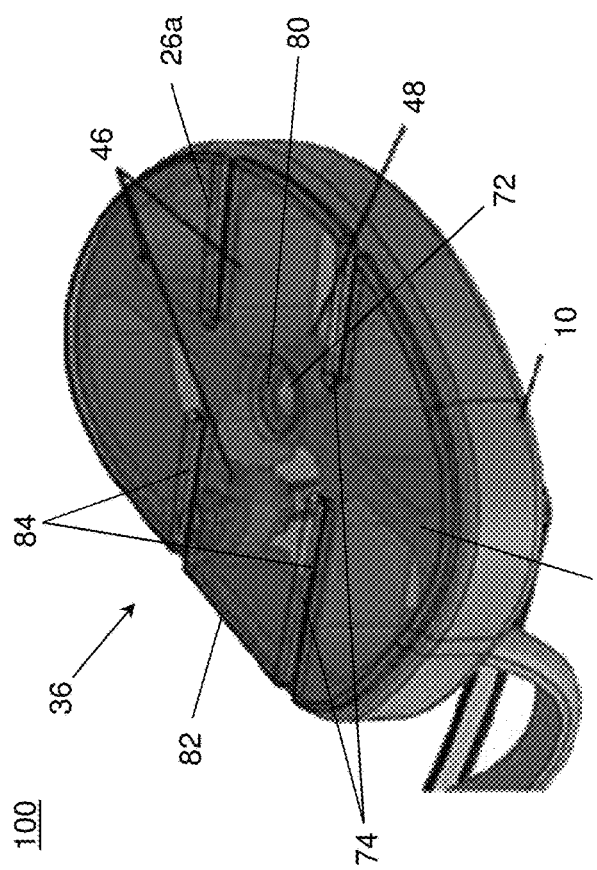
FIG. 18 is a perspective view of a nasal dilator with a diaphragm valve having slits and seated on longitudinal and lateral spars.

An embodiment of the NED device which uses different types of a diaphragm valve 48 is shown in FIGS. 15A and 15B and FIG. 18. FIGS. 15A and 15B shows the housing 10 as an elongated tube 22, and the seat 12 is formed by angled spars 26. In the closed configuration 36, the diaphragm valve 48 expands and is pushed against the angled spars 26 by the exhalation airflow to create the backpressure. In the open configuration 34, the flaps 46 of the diaphragm valve 48 are nearly aligned with the housing's central longitudinal axis 42 which allows the inhalation airflow to freely pass through the interior space of the housing. FIG. 18 is a planar frame 24 version of the NED device with a diaphragm valve 48 that has a central mount 72 and slits 74. The slits 74 provide additional flexibility to promote inhalation airflow. In this embodiment, the seat is formed by intersecting lateral spars 26a and longitudinal spars 26b. The central mount can be a separate structure with a mechanical connection to the seat or it can be integrally formed with the seat or it may be otherwise adhered or fused to the seat.

Regardless of the connection formed by the mount between the valve and either the seat or the housing, the mount is on the outer side of the valve, preferably connected directly to the seat, and no part of the mount nor any anchoring stem extends into the interior space of the housing on the inner side of the valve. Additionally, there is no bulbous retaining prong on the inner side of the valve. The absence of the anchoring stem and retaining prong structures or any other structure in the interior space of the housing on the inner side of the valve allows the valve to fold flatter than would otherwise be possible with a structure that extends into the interior space and the flatter fold improves the inhalation airflow through the valve by minimizing the resistance to the airflow.

The embodiment of the NED device shown in FIGS. 16A and 16B has a duck valve 54 that operates by resting on angled spars 26 that meet at a point within the interior of the housing 10. Again, as explained above, the spars are on the outer side of the valve and do not extend into the interior space of the housing on the inner side of the valve. As with the other types of seat mechanisms described herein, the angled spars 26 prevent the duck valve's flaps 54 from being forced into the blow-through position. In the closed configuration, shown in FIG. 16A, the exhalation airflow forces the valve onto the supporting seat, and the closed configuration produces backpressure. In the open configuration 34, shown in FIG. 16B, the duck valve flaps 54 open to a near alignment with the housing's central axis allowing the inhalation airflow to move freely with minimal resistance.

The embodiment of the NED device shown in FIGS. 17A and 17B has an umbrella valve 52 and a screen 28. During exhalation, the umbrella valve 52 spans across the interior of the housing 10 covering the bottom and rests upon the screen 28 closing off the airflow. In FIG. 17B, in the open configuration 34 during inhalation, the umbrella valve 52 folds together so that its flaps 46 are nearly aligned with the housing's central longitudinal axis 42 allowing the inhalation airflow to move freely with minimal resistance.

Figure 20:
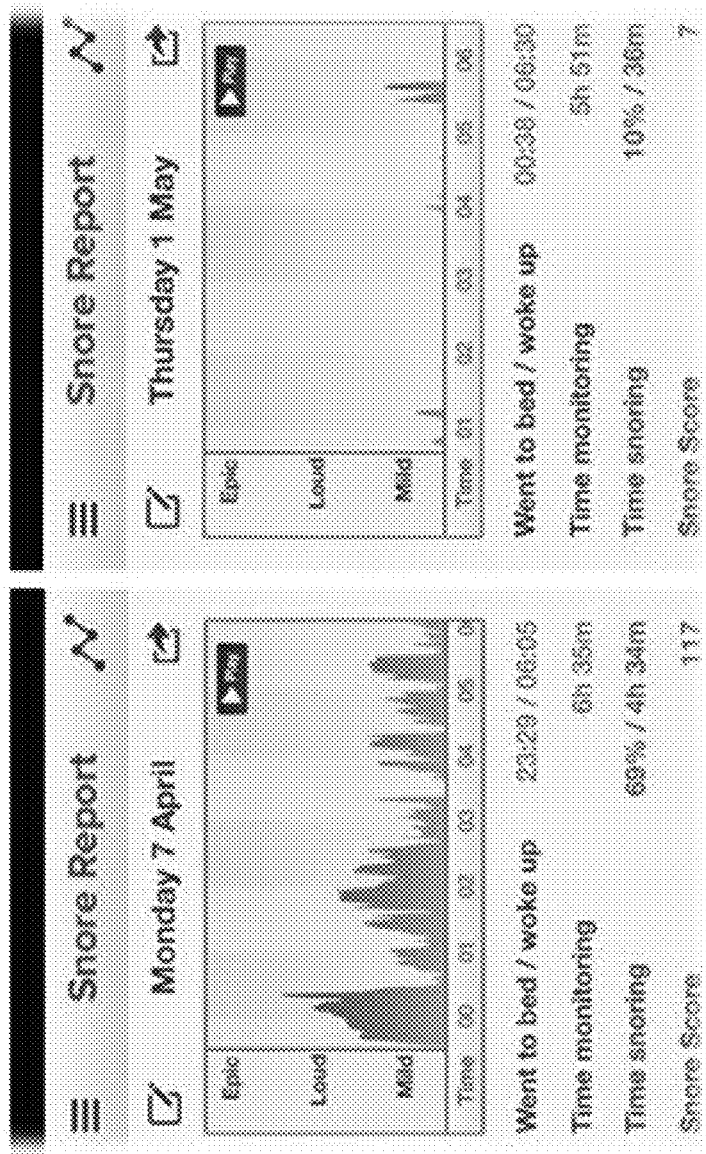
FIG. 20 illustrates an example snore report showing a time history of a person's sleep without any nasal device and with the nasal dilator and valve device according to the present invention.

According to the embodiments of the NED device described above and shown in the accompanying drawings, any obstruction of airflow during inhalation by the valves 14 is more than offset by the dilation of the nasal passageway by the housing. Accordingly, insertion of the NED device expands the effective nasal airway passage available during inhalation, in comparison to inhalation without any device at all creating a net increase of airflow. The minimal airflow resistance of the open valve is inconsequential and more than overcome by reduced resistance resulting from the dilation of the nasal passageway that is produced by the housing such that the inhalation airflow through the nasal passageway with the NED device 100 is greater than the unaided inhalation airflow through the nasal passageway without the NED device (QNEDinhalation>QUnaidedInhalation)). As explained above, the NED device's valve restricts the exhalation airflow to create a backpressure (QNEDexhalation<QUnaidedExhalation) & QNEDexhalation<QNEDinhalation), and the seat prevents the blowout condition with the blow-through of the valve by providing a stop mechanism that spans the interior space of the housing on the outer side of the valve. As shown in FIG. 19, blowout can occur in the prior art nasal EPAP devices which do not provide a seat that spans the interior space of the housing. FIG. 20 is an example of a report displaying the effects of the present NED device and its benefits. The graph on the left is an example without the NED device, baseline 56b, and the graph on the right is with the nasal dilator and valve device according to the present invention, i.e., the dilated nasal passageway 56a with the NED device. As shown, the time snoring is significantly decreased illustrating the benefit of the present NED device. One novel, and significant, aspect of most embodiments of the present invention are their incorporation of differing forms of differentia valves within the nasal dilator housing, so that separate, reinforcing effects can be achieved with the use of a single simple implement. Collectively, the embodiments of the present invention are referred to as Nasal EPAP (Expiratory Positive Airway Pressure) Dilators, or NEDs. The NED embodiments incorporate a pair of nasal dilator housings, which expand the nasal passageway and have walls of sufficient strength to maintain the dilation even during inhalation, when the nasal passageway normally narrows. Spanning the space that passes between the NED housing walls are differential valves, which operate differently when the air flow is in the inhalation direction than when the airflow is in the exhalation direction. Frequently, the valve is composed of a form of flap, often constructed of a silicone compound that is sufficiently thin to be readily curled, folded, or forced back to open up an air passage. It has also been found that those with mild to moderate SDB issues can benefit from the addition of simple nasal dilation to OAT, and can sometimes be satisfied with that level of performance alone, though the effect is insufficient for those having greater degrees of difficulty. Many embodiments of the present invention reflect a synthesis of the understandings of the potential for differential inhalation/exhalation inhibiting nasal therapies to beneficially supplement OAT along with novel approaches to avoiding the comfort issues of the existing therapies, plus combining these insights with a significantly different approach to shaping air passage pressure levels. These present embodiments involve an intranasal device that combines nasal passage dilators with a non-way valve to distinguish between exhalation and inhalation effects. The one-way valve is integrated into the dilator housing, so that the application of the (nasal therapy) device simply involves insertion of a pair of nasal dilator assemblies by holding their connecting bridge component. The dilator housings are shaped to fit comfortably, yet snuggly, within the nasal passage and when inserted they substantially open the passageways and maintain these opening expansions when inhalation occurs, wherein the nasal passageway normally narrows when inhaling, often substantially. This approach is diametrically opposed in methodology to the existing nasal therapies that also effect differing inhalation and exhalation effects. These existing approaches always increase pressure, but they differentiate between exhalation and inhalation by attempting less inhibition during inhalation. By contrast, most embodiments of the present invention not only don't inhibit inhalation at all, but actually increase inhalation ease by dilating the nasal passage and maintaining that dilation during inhalation rather than allowing the normal narrowing of the nasal passage. Due to their manners of use, the prior approaches cannot ease inhalation even in principle, and in practice most restrict inhalation at least somewhat. In the particular features and operation of the NED device, the housing includes a perimeter wall which defines the extent of the housing in the plane perpendicular to the nasal air flow, and whose spread in the direction of the nasal air flow both defines a channel for the nasal air flow and enacts a dilating effect for the nasal passage by defining an internal nasal air passageway that is greater than occurs normally without the presence of the NED device.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A nasal dilator for a nasal passageway to prevent a constriction therein, comprising:
   a housing, wherein the housing is comprised of sidewalls with an interior surface, an exterior surface, an inner end, and an outer end, wherein the interior surface has opposing sides surrounding an interior space and extending between the inner end and the outer end, wherein the exterior surface is configured to be positioned within the nasal passageway, wherein the housing expands the nasal passageway from a baseline state without the housing inserted in the nasal passageway to a dilated state with the housing inserted in the nasal passageway, and wherein the sidewalls produce a dilation of the nasal passageway in the dilated state with the interior space of the housing being greater than the constriction of the nasal passageway in the baseline state;
   a seat connected to the opposing sides of the housing's interior surface at a first location, wherein the seat spans the interior space, and wherein the first location is situated between the inner end and the outer end of the housing; and
   a valve connected to at least one of the seat and the housing at a second location between the first location and the inner end of the housing, wherein the valve has an open configuration when an inhalation airflow passes from the outer end to the inner end and a closed configuration when an exhalation airflow passes from the inner end to the outer end, wherein the valve is the only structure extending beyond the second location into the interior space when the valve is in the open configuration, wherein the seat supports the valve in the closed configuration, wherein the valve is configured to restrict the exhalation airflow in the closed configuration, and wherein the dilation in the nasal passageway and the open configuration of the valve create less restriction for the inhalation airflow to pass through the interior space of the housing in the dilated state than an unaided inhalation airflow which passes through the nasal passageway in the baseline state without the housing with the valve.

2. The nasal dilator of claim 1, further comprising a bridge connecting the housing to a second housing containing a second seat and a second valve, wherein the bridge is at least one of a detachable bridge and an integral bridge.

3. The nasal dilator of claim 2, further comprising a second bridge connecting the housing to the second housing, wherein the bridge is a flexible integral bridge, and wherein the second bridge is a rigid detachable bridge.

4. The nasal dilator of claim 1, wherein no structure extends into the interior space of the housing beyond the second location other than the valve in the open configuration.

5. The nasal dilator of claim 1, wherein the housing has a length between the inner end and the outer end and has a distance between the opposing sides, wherein the housing is further comprised of at least one of an elongated tube and a planar frame, wherein the length of the elongated tube is longer than the distance between the opposing sides, and wherein the length of the planar frame is shorter than the distance between the opposing sides.

6. The nasal dilator of claim 1, wherein the housing is comprised of an elongated tube, wherein a length between the inner end and the outer end of the elongated tube is longer than a distance between opposing sides of the elongated tube, and wherein no structure other than the valve is in the interior space of the housing between the inner end and the outer end of the elongated tube.

7. The nasal dilator of claim 1, wherein the valve is further comprised of at least one of a flap valve, a diaphragm valve, a hinged disc valve, an umbrella valve, and a duck valve, wherein the housing has a central longitudinal axis, wherein a first section of the valve is connected to at least one of the seat and the housing, wherein a second section of the valve extends to a free end of the valve, and wherein the second section bends and the free end is approximately aligned with the central longitudinal axis when the inhalation airflow pushes the valve into the open configuration.

8. The nasal dilator of claim 1, wherein the housing is comprised of a planar frame, wherein the seat is comprised of a plurality of lateral spars extending across the interior space between a first pair of the opposing sides and a longitudinal spar extending across the interior space between a second pair of the opposing sides and intersecting with the lateral spars, wherein the valve is comprised of a plurality of flaps, and wherein each of the flaps has a fixed end connected to the opposing sides, and a pair of sides extending to a free end in the interior space between the opposing sides.

9. The nasal dilator of claim 1, further comprising a mount connecting the valve to at least one of the seat and the housing, wherein no portion of the mount extends into the interior space of the housing beyond the second location.

10. The nasal dilator of claim 1, wherein the seat produces a valve stop in the closed configuration and prevents a blow-through of the valve from the second location to the outer end of the housing when the exhalation airflow passes through the housing.

11. A nasal dilator for a nasal passageway to prevent a constriction therein, comprising:
   a housing, wherein the housing is comprised of sidewalls with an interior surface, an exterior surface, an inner end, and an outer end, wherein the interior surface has opposing sides surrounding an interior space and extending between the inner end and the outer end, wherein the exterior surface is configured to be positioned within the nasal passageway, wherein the housing expands the nasal passageway from a baseline state without the housing inserted in the nasal passageway to a dilated state with the housing inserted in the nasal passageway, and wherein the sidewalls produce a dilation of the nasal passageway in the dilated state with the interior space of the housing being greater than the constriction of the nasal passageway in the baseline state;
   a seat connected to the opposing sides of the housing's interior surface at a first location, wherein the seat spans the interior space, and wherein the first location is situated between the inner end and the outer end of the housing; and
   a valve connected to at least one of the seat and the housing at a second location between the first location and the inner end of the housing, wherein the valve has an open configuration when an inhalation airflow passes from the outer end to the inner end and a closed configuration when an exhalation airflow passes from the inner end to the outer end, wherein the valve is the only structure extending beyond the second location into the interior space when the valve is in the open configuration, wherein the seat supports the valve in the closed configuration, and wherein the valve is configured to restrict the exhalation airflow in the closed configuration;
   wherein the dilation in the nasal passageway and the open configuration of the valve create less restriction for the inhalation airflow to pass through the interior space of the housing in the dilated state than an airflow which passes through the nasal passageway in the baseline state without the housing with the valve; and
   wherein the seat produces a valve stop in the closed configuration and prevents a blowthrough of the valve from the second location to the outer end of the housing when the exhalation airflow passes through the housing.

12. The nasal dilator of claim 11, further comprising a bridge connecting the housing to a second housing containing a second seat and a second valve, wherein the bridge is at least one of a detachable bridge and an integral bridge, wherein the housing is further comprised of a bridge receiver, wherein the bridge is rigid and is detachably connected to the bridge receiver.

13. The nasal dilator of claim 11, no structure other than the valve extends into the interior space of the housing beyond the second location.

14. The nasal dilator of claim 11, wherein the housing has a length between the inner end and the outer end and has a distance between the opposing sides, wherein the housing is further comprised of at least one of an elongated tube and a planar frame, wherein the length of the elongated tube is longer than the distance between the opposing sides, wherein the length of the planar frame is shorter than the distance between the opposing sides, wherein the seat is comprised of at least one of a spar and a screen, and wherein the valve is further comprised of at least one of a flap valve, a diaphragm valve, a hinged disc valve, an umbrella valve, and a duck valve, wherein the housing has a central longitudinal axis, wherein a first section of the valve is connected to at least one of the seat and the housing, wherein a second section of the valve extends to a free end of the valve, and wherein the second section bends and the free end is approximately aligned with the central longitudinal axis when the inhalation airflow pushes the valve into the open configuration.

15. The nasal dilator of claim 11, wherein the housing is comprised of an elongated tube, wherein a length between the inner end and the outer end of the elongated tube is longer than a distance between opposing sides of the elongated tube, and wherein no structure other than the valve is in the interior space of the housing between the inner end and the outer end of the elongated tube.

16. A nasal dilator for a pair of nasal passageways to prevent a corresponding pair of constrictions therein, comprising:
   a first housing;
   a first seat connected to the first housing;
   a first valve connected to the first housing;
   a second housing;
   a second seat connected to the second housing;
   a second valve connected to the second housing; and
   a bridge connecting the first housing to the second housing; wherein each one of the first housing and the second housing is comprised of sidewalls with an interior surface, an exterior surface, an inner end, and an outer end, wherein the interior surface has opposing sides surrounding an interior space and extending between the inner end and the outer end, wherein the exterior surface for the first housing and the second housing are configured to respectively be positioned within the nasal passageways, wherein the first valve and the second valve each has an open configuration when an inhalation airflow passes from the outer end to the inner end and a closed configuration when an exhalation airflow passes from the inner end to the outer end, wherein the first valve and the second valve are the only structures within the interior space of the first housing and the second housing, respectively, in the open configuration; and
   a bridge connecting the first housing to a second housing, wherein the bridge is at least one of a detachable bridge and an integral bridge.

17. The nasal dilator of claim 16, wherein each one of the first seat and the second seat is connected to the opposing sides of the respective interior surface of the first housing and the second housing at a first location, wherein the first seat and the second seat respectively span the interior space of the first housing and the second housing, wherein the first location is situated between the inner end and the outer end, wherein each one of the first valve and the second valve is connected to the respective one of the first housing and the second housing at a second location between the first location and the inner end, wherein the first seat and the second seat respectively support the first valve and the second valve in the closed configuration, and wherein each one of the first valve and the second valve is configured to restrict the exhalation airflow in the closed configuration, wherein no portion of any structure other than the first valve and the second valve extends into the interior space of the first housing and the second housing beyond the second location.

18. The nasal dilator of claim 16, wherein the first housing expands one of the nasal passageways from a baseline state without the first hosing inserted in a first one of the nasal passageways to a dilated state with the first housing inserted in the first nasal passageway, wherein the sidewalls of the first housing produce a first dilation of the first nasal passageway in the first dilated state with the interior space of the first housing that is greater than the corresponding one of the constrictions of the first nasal passageway in the first baseline state, wherein the second housing expands a second one of the nasal passageways from a second baseline state without the second housing inserted in the second nasal passageway to a second dilated state with the second housing inserted in the second nasal passageway, and wherein the sidewalls of the second housing produce a second dilation of the second nasal passageway in the second dilated state with the interior space of the second housing that is greater than the corresponding other one of the constrictions of the second nasal passageway in the second baseline state.

19. The nasal dilator of claim 16, wherein the first housing and the second housing is each further comprised of a bridge receiver, wherein the bridge is rigid and is detachably connected to the bridge receiver, and wherein the valve is attached to the seat and is connected to the housing through the seat.

20. The nasal dilator of claim 16, wherein the first housing and the second housing are comprised of an elongated tube, wherein a length between the inner end and the outer end of the elongated tube is longer than a distance between opposing sides of the elongated tube, and wherein no structure other than the valve is in the interior space of the housing between the inner end and the outer end of the elongated tube.

* * * * *